(12) United States Patent
Abe et al.

(10) Patent No.: US 6,200,313 B1
(45) Date of Patent: Mar. 13, 2001

(54) PUNCTURE INSTRUMENT FOR PUNCTURED HIGH FREQUENCY TREATMENTS

(75) Inventors: Kenji Abe; Mituo Kondo, both of Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 0 days.

(21) Appl. No.: 08/847,247

(22) Filed: May 1, 1997

Related U.S. Application Data (63) Continuation of application No. 08/388,436, filed on Feb. 14, 1995, now abandoned.

(30) Foreign Application Priority Data

Mar. 31, 1994 (JP) .................................................. 6-083712

(51) Int. Cl.[7] .................................................. A61B 18/14
(52) U.S. Cl. .................................. 606/34; 606/39; 606/46
(58) Field of Search ........................ 606/32–52; 600/107; 607/154, 158, 164; 604/20–22, 27

(56) References Cited

U.S. PATENT DOCUMENTS

| | | | |
|---|---|---|---|
| 1,952,617 | * 3/1934 | Wappler | 606/46 |
| 2,484,059 | * 10/1949 | Wallner | 606/46 |
| 4,724,836 | * 2/1988 | Okada | 606/46 |
| 4,950,267 | * 8/1990 | Ishihara et al. | 606/15 |
| 5,277,696 | * 1/1994 | Hagen | 606/45 |
| 5,370,675 | * 12/1994 | Edwards et al. | 606/32 |
| 5,403,311 | * 4/1995 | Abele et al. | 606/48 |
| 5,423,848 | * 6/1995 | Washizika et al. | 606/45 |
| 5,462,521 | * 10/1995 | Brucker et al. | 606/46 |

FOREIGN PATENT DOCUMENTS

9315664 * 8/1993 (WO) ................................... 606/49

* cited by examiner

*Primary Examiner*—David M. Shay
(74) *Attorney, Agent, or Firm*—Oblon, Spivak, McClelland, Maier & Neustadt, P.C.

(57) ABSTRACT

A puncture instrument capable of punctured high frequency treatments. The puncture instrument essentially includes: a guide tube to be inserted into an intracavitary portion of a patient; a puncture needle member having an elongated needle body slidably received in the guide tube, and a sharp-pointed needle head provided contiguously at the fore end of the elongated needle body and protrudable out of the guide tube to penetrate into a target intracorporeal portion to be treated when the needle body is manipulated in a forward direction; and a high frequency electrode provided on a fore end portion of the needle body to be penetrated into the target intracorporeal portion together with the sharp-pointed needle head.

8 Claims, 9 Drawing Sheets

PUNCTURE INSTRUMENT FOR PUNCTURED HIGH FREQUENCY TREATMENTS

This application is a Continuation of application Ser. No. 08/388,436, filed on Feb. 14, 1995, now abandoned.

BACKGROUND OF THE INVENTION

1. Field of the Art

This invention relates generally to a medical puncture instrument, and more particularly to a puncture instrument for punctured high frequency treatments, having a high frequency electrode on a puncture needle member to be driven into a target organ or tissues in an intracorporeal region of a patient for a high frequency treatment.

2. Description of the Prior Art

For instance, ultrasound endoscopes are widely resorted to in the medical fields not only for intracorporeal examinations and diagnosis but also for therapeutic purposes to give an appropriate treatment to a diseased portion on the basis of the results of an examination or diagnostic observation. In many cases, the ultrasound endoscopes of this sort are provided with an ultrasound imaging means along with an endoscopic observation means at the fore end of a catheter-like insert portion to be introduced into an intracavitary portion of a patient. The endoscopic observation means is suitable for examinations of conditions of intracavitary walls, while the ultrasound observation means is suitable for examinations of tissues in deeper intracorporeal regions. In case a diseased portion is spotted by any of these examinations, there arises a necessity for inserting a therapeutic instrument for the treatment of the diseased portion. For this purpose, the ultrasound endoscopes are usually provided with the so-called biopsy channel which is designed to guide a bioptic or therapeutic instrument to be inserted into a particular intracorporeal portion under observation through the endoscopic or ultrasound imaging means. Some bioptic or therapeutic instruments are inserted into and manipulated through a biopsy channel on an endoscope for the treatment of a certain intracorporeal portion, as in the case of forceps and high frequency therapeutic instruments which are used for sampling intracavitary wall tissues or for coagulation or hemorrhage control treatments. On the other hand, it has been known in the art to penetrate a puncture instrument into an intracorporeal organ or tissues of interest through an intracavitary wall for injection of a medicinal liquid or for an aspiratory or suctional drainage treatment.

In this connection, conventional instruments designed for high frequency therapeutic treatments within an intracavitary tract, for example, are unable to treat cancer cells or other diseased portions which exist underneath the mucous membrane. On the other hand, conventional puncture needles are designed to serve for a treatment of a specific nature such as injection of a medicinal liquid or suctional evacuation of a diseased portion, and thus have only a limited range of application, precluding applications to other treatments like high frequency treatments.

SUMMARY OF THE INVENTION

Under these circumstances, it is a primary object of the present invention to provide a puncture instrument capable of performing a high frequency treatment such as a high frequency coagulation or high frequency incision treatment on a diseased portion in an intracorporeal region of a patient in a secure and reliable manner.

In accordance with the invention, the above-stated objective is achieved by the provision of a puncture instrument capable of punctured high frequency treatments, the puncture instrument essentially including: a guide tube to be inserted into an intracavitary portion of a patient; a puncture needle member having an elongated needle body slidably received in the guide tube, and a sharp-pointed needle head provided contiguously at the fore end of the elongated needle body and protrudable out of the guide tube to penetrate into a target intracorporeal portion to be treated; and a high frequency electrode provided on a fore end portion of the needle body for penetration into the intracorporeal portion together with the sharp-pointed needle head.

In order to introduce the puncture instrument into an intracorporeal portion which needs a high frequency treatment, for example, by using an ultrasound endoscope as a guide means, firstly the instrument is inserted into a biopsy channel of an endoscope with the puncture needle in a retracted position within the guide tube. As soon as the tip end of the endoscope reaches an intracavitary portion of interest, the puncture instrument is protruded from the biopsy channel to abut the fore end of the guide tube against an intracavitary wall portion to be penetrated by the puncture needle member. Then, the puncture needle member is driven into a target intracroporeal portion where the high frequency electrode is positioned in face to face relation with the diseased portion. In this state, high frequency current is applied to the electrode to give the diseased portion a high frequency treatment such as a high frequency coagulation treatment or a high frequency incision treatment which makes a cut by evaporation of tissues.

The above and other objects, features and advantages of the invention will become apparent from the following description, taken in conjunction with the accompanying drawings which show by way of example a number of preferred embodiments of the invention.

DESCRIPTION OF PREFERRED EMBODIMENTS

Hereafter, the invention is described more particularly by way of its preferred embodiments with reference to the accompanying drawings. In various embodiments shown in the drawings, the puncture instrument of the invention is adapted for use with an ultrasound endoscope which serves as a guide means for the puncture instrument. However, it is to be understood that the guide means for the insertion of the puncture instrument is not limited to an ultrasound endoscope which is shown as one example of guide means.

Figure 1:
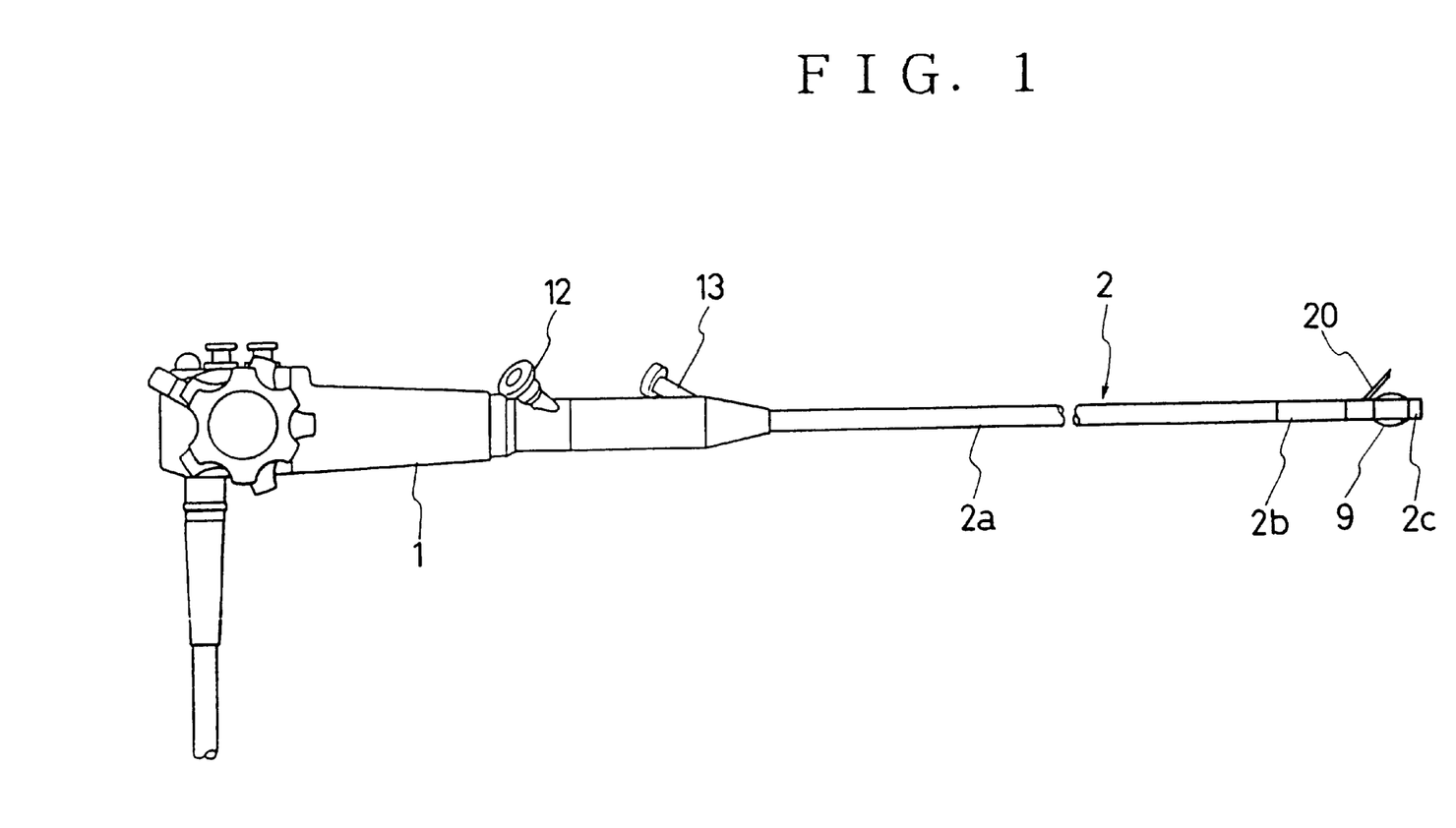
FIG. 1 is a partly cutaway schematic view of an ultrasound endoscope suitable for use with the puncture instrument according to the invention.

Referring first to FIG. 1, there is shown the general configuration of an ultrasound endoscope, in which indicated at 1 is a main body with manipulating control means for the ultrasound endoscope, and at 2 is a catheter member which is extended out from the main body 1 for insertion into an intracavitary portion to be examined. The catheter member 2 is composed of a flexible section 2a, which extends nearly over the entire length of the catheter member 2 except an angle section 2b which is connected to the fore end of the flexible section 2a, and a rigid fore end section 2c which is connected to the angle section 2b to form the tip end of the catheter member 2.

Figure 2:
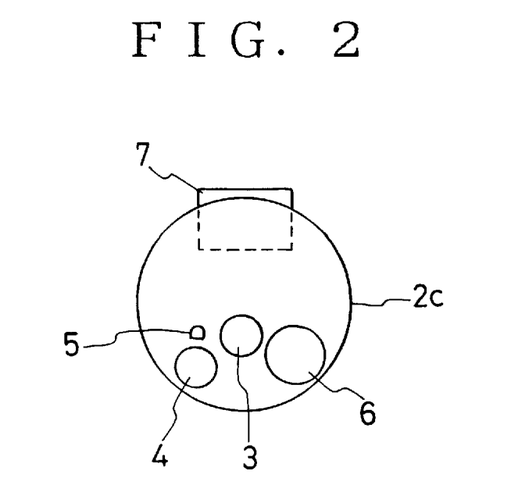
FIG. 2 is a schematic end view of a rigid fore end portion of the ultrasound endoscope of FIG. 1.
Figure 3:
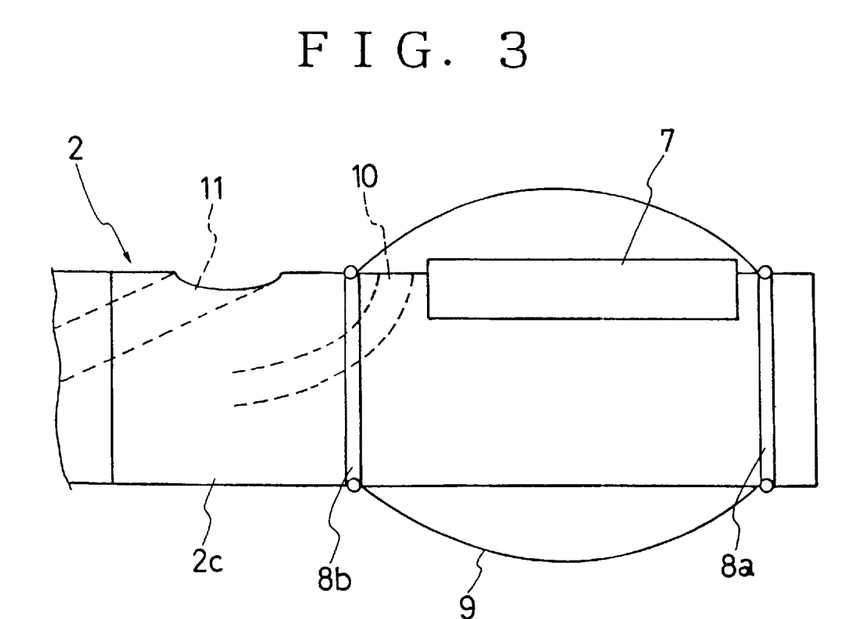
FIG. 3 is a partly sectioned side view of the rigid fore end portion of the ultrasound endoscope.

Shown in FIGS. 2 and 3 is the construction of the above-mentioned rigid fore end section 2c, which supports thereon an endoscopic observation means and an ultrasound imaging means. The endoscopic observation means includes an illumination window 3 and an observation window 4 which are provided on the distal end face of the rigid fore end section 2c. As well known in the art, an illuminating lens is fitted in the illumination window 3 in front of the light emitting end of a light guide which is extended through the catheter member 2. On the other hand, fitted in the observation window 4 is an objective lens to form optical images on a plane where a solid-state image sensor or the light incident end of an image guide is located. In addition to these windows, an air/water feed nozzle 5 is provided on the distal end face of the rigid fore end section 2c for the purpose of washing the observation window 4, along with an exit opening of a biopsy channel 6 which serves as a guide channel for insertion of forceps or other instruments.

The above-mentioned ultrasound imaging means includes an ultrasound transducer 7 which is mounted on a lateral side of the rigid fore end section 2c, and a pair of annular grooves 8a and 8b which are formed on the front and rear sides of the ultrasound transducer 7 to anchor therein opposite end portions of a balloon 9 in a fluid-tight state. Opened on the front side of the balloon anchoring groove 8b is a passage 10 through which the balloon 9 is supplied with an ultrasound transmissive medium. A puncture instrument guide channel 11 is opened on the proximal side of the balloon anchoring groove 8b on the proximal side of the ultrasound transducer 7, namely, outside the balloon fitting area of the rigid fore end section 2c, to guide therethrough the puncture instrument to be penetrated into an intracorporeal portion.

A bioptic or therapeutic instrument which has been passed through the biopsy channel 6 is normally manipulated under observation through the endoscopic observation means. Therefore, the biopsy channel 6 is opened on the distal end face of the rigid fore end section 2c, allowing to capture the instrument always within the view field of the endoscopic observation means when protruded into an intracavitary portion from the distal end of the rigid fore end section 2c of the catheter member 2. On the other hand, the puncture instrument, to be penetrated into a deeper intracorporeal portion, needs to be manipulated under the guidance of ultrasound images produced by the ultrasound transducer 7. Accordingly, in order to hold the puncture instrument within the view field of the ultrasound imaging means, the puncture needle guide channel 11 is so arranged as to protrude the puncture instrument into the view field of the ultrasound transducer 7 from a position immediately on the proximal or near side of the transducer 7. Both of biopsy channel 6 and the puncture instrument guide channel 11 are extended through the catheter member 2 from separate entrance openings 12 and 13 on the main body 1 of the endoscope, respectively.

FIGS. 4 through 12 show various embodiments of the puncture instrument of the invention.

Figure 5:
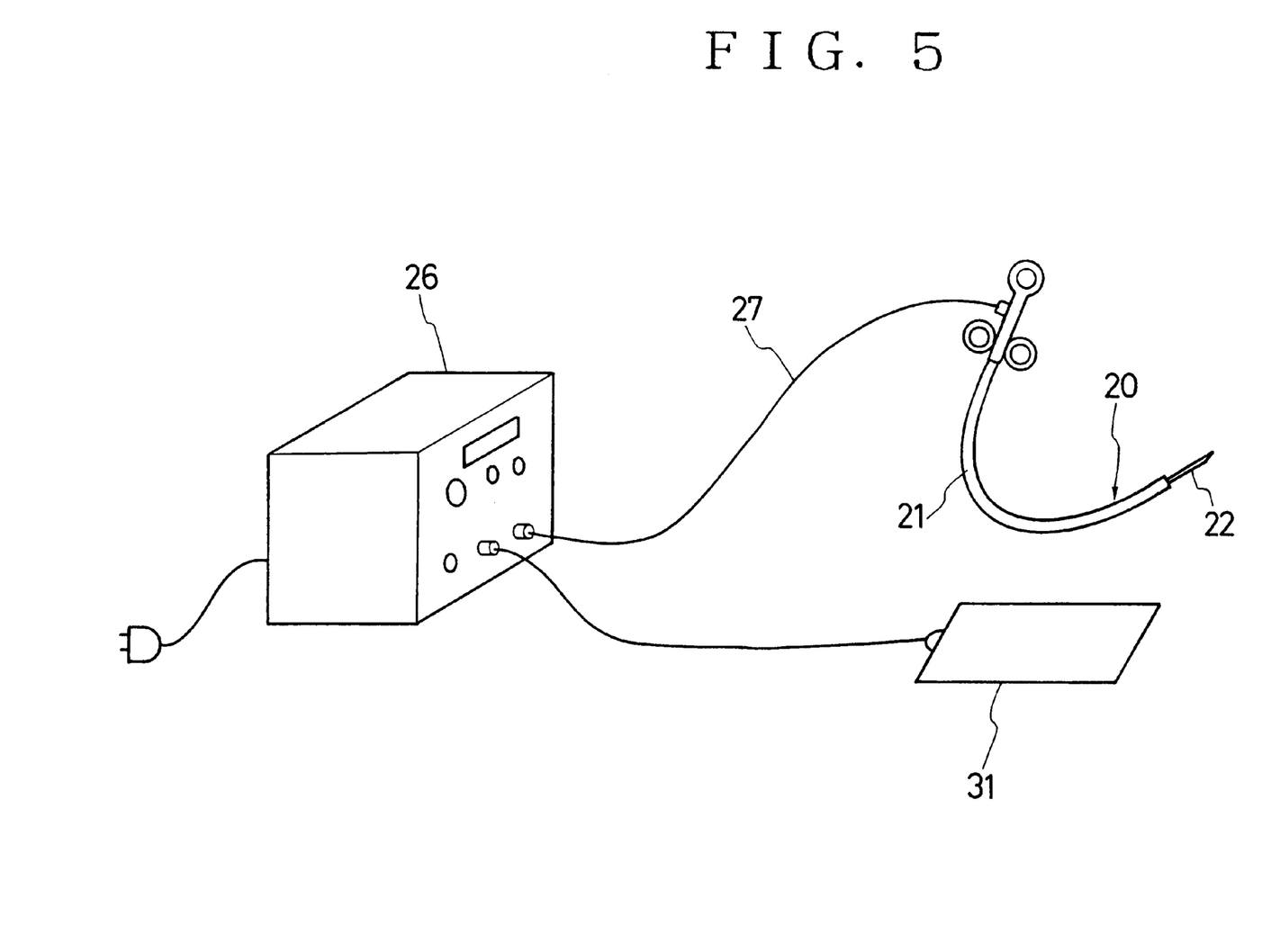
FIG. 5 is a schematic view of a high frequency treatment system employing the puncture instrument of the invention.
Figure 6:
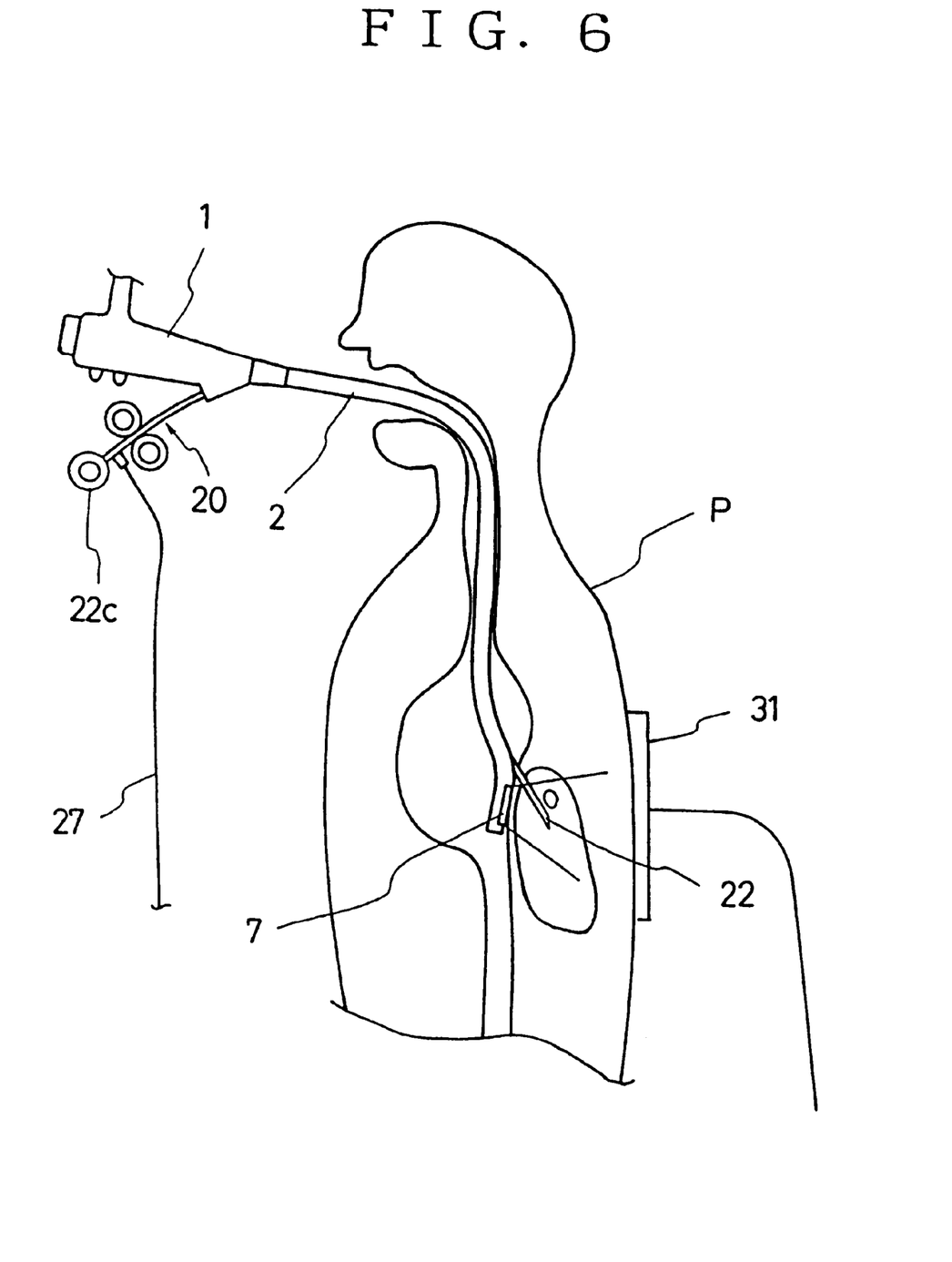
FIG. 6 is a schematic illustration of a high frequency treatment by the puncture instrument, monitoring the puncture operation through ultrasound imaging means.
Figure 9:
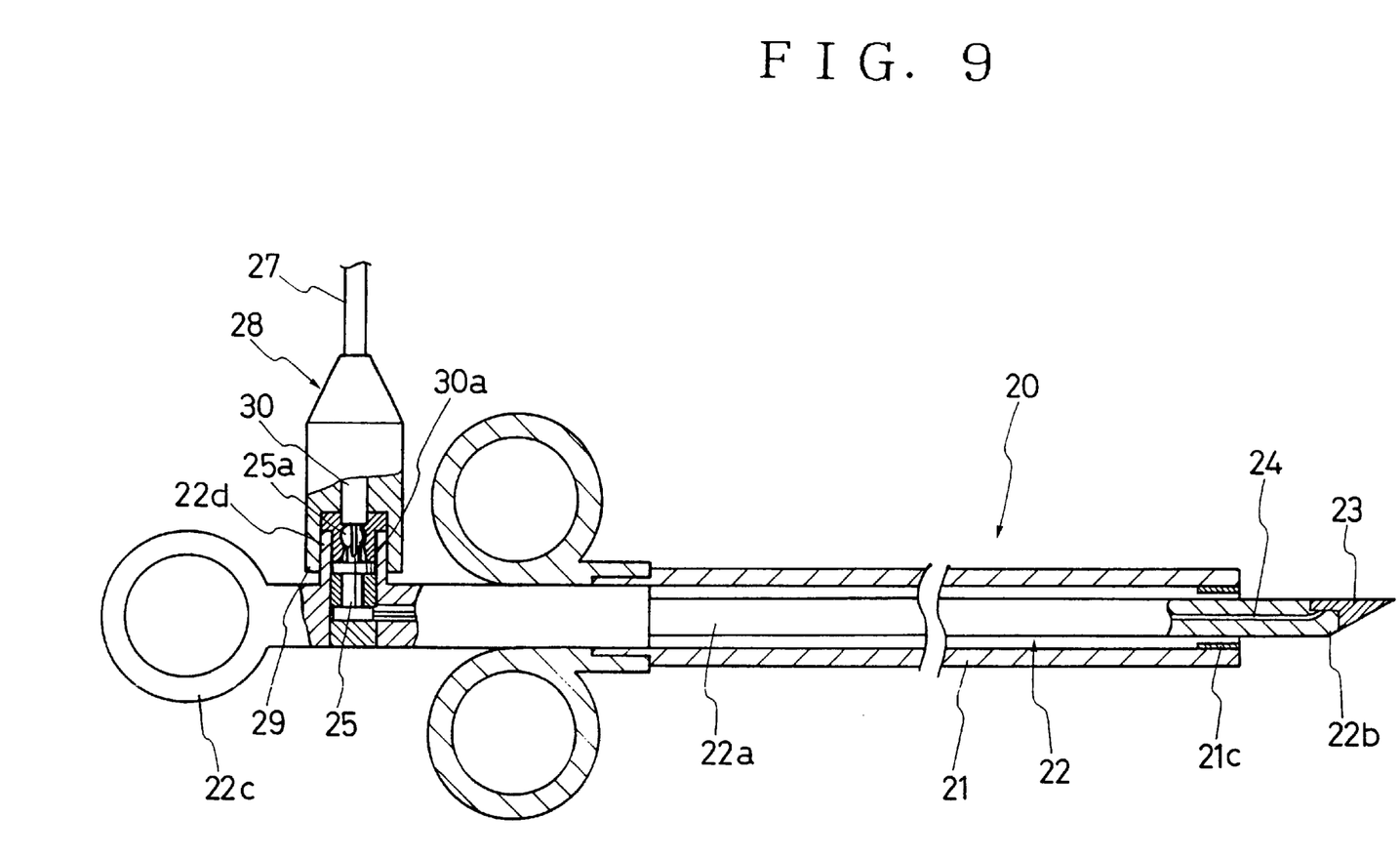
FIG. 9 is a partly sectioned schematic view of a further embodiment of the puncture needle of the invention.

Illustrated in FIGS. 5, 6 and 9 is on embodiment of the invention, where indicated at 20 is a puncture instrument including a flexible guide tube 21, which is formed of an electrically insulating synthetic resin material and open at the opposite ends thereof, and an elongated puncture needle member 22 slidably fitted in the guide tube 21. As shown in FIG. 9, the puncture needle member 22 is constituted by a flexible needle body 22a, a sharp-pointed needle head 22b integrally connected to the fore end of the needle body 22a, and a grip portion 22c provided at the proximal tail end of the needle body 22a. This puncture needle member 22 is also formed of an insulating synthetic resin material except the sharp-pointed head 22b at the fore end of the needle body, 22a which serves as a high frequency electrode 23.

The sharp-pointed head 22b of the puncture needle member 22 is normally held in a retracted position within the guide tube 21, and, upon pushing inward the grip 22c with a finger or fingers, it is protruded over a predetermined length from the fore end of the guide tube 21 to assume an operative position. A metal ring 21c is fixedly fitted at the fore end of the guide tube 21 in such a position as to circumvent the high frequency electrode 23 of the puncture member 22 when the latter is in the retracted position.

A wiring cable 24 from the high frequency electrode 23 is passed through the flexible needle body 22a and connected at its proximal end to a contact pin 25 of a connection terminal 22d which is provided on the needle body 22a on the front side of the grip portion 22c. The connection terminal 22d is provided with a cylindrical member which is disposed perpendicular to the axis of the flexible needle body 22a, housing the contact pin 25 therein. In the particular embodiment shown, the contact pin 25 is constituted by a split resilient rod-like member with a spherical head 25a at the fore end thereof.

In FIG. 5, denoted at 26 is a high frequency power source which is provided with a connector 28 (FIG. 9) at the distal end of its high frequency current supply cable 27. A connector pin 30 which is disconnectibly connectible to the afore-mentioned contact pin 25 on the main body of the endoscope is provided within a cylindrical insulating cover 29 of the connector 28. The connector pin 30 is formed in a cylindrical shape and provided with clasping ribs 30a on the inner periphery thereof. Therefore, upon fitting the cylindrical cover 29 of the connector 28 on the connection terminal 22d on the part of the endoscope, the connector pin 30 is fittingly coupled with the contact pin 25 to establish electrical connection therebetween. Further, a counter electrode plate 31 (FIGS. 5 and 6) to be held against the body of a patient is also connected to the high frequency power source 26.

In a high frequency treatment by the use of the puncture instrument of the above-described arrangements, for example, while holding the counter electrode plate 31 against the back of a patient P (FIG. 6), the catheter member 2 of the ultrasound endoscope is perorally introduced into the digestive tract of the patient to locate its rigid fore end section 2c in a stomach region to be examined. In this state, the stomach wall condition is examined through the endoscopic observation means and, if necessary, the transducer 7 of the ultrasound imaging means is actuated to obtain the information of intracorporeal tissues in a particular region of interest by ultrasound scanning. In case cancer cells or other diseased portion is spotted from ultrasound images produced by the ultrasound observation means, the puncture instrument 20 is driven forward to penetrate the needle head 22b into the diseased portion for a high frequency treatment such as a high frequency coagulation or high frequency incision treatment.

In this instance, the puncture needle member 22 is held in a retracted position within the guide tube 21 at the time of inserting the puncture instrument into the guide passage 11 on the ultrasound endoscope. The puncture instrument is normally kept from protruding out of the rigid fore end section 2c of the catheter member 2 while the ultrasound endoscope is being used for an examination or diagnosis through the endoscopic observation means or the ultrasound imaging means. In case a diseased portion is spotted by the ultrasound observation means, the puncture instrument 20, including the guide tube 21, is protruded out of the puncture instrument guide channel 11 until the fore end of the guide tube 21 is abutted against an intracavitary wall in front of the diseased portion. In this state, the grip 22c is pushed toward the guide tube 21, urging the puncture needle member 22 to slide forward within the guide tube 21 to penetrate the needle 22b head through the intracavitary wall toward the diseased portion. This penetrating operation by the puncture needle member 22 is monitored by way of the ultrasound images from the ultrasound imaging means to ensure that the needle head 22b be penetrated toward the diseased portion securely and safely.

As soon as the high frequency electrode 23 at the head of the puncture needle member 22 reaches an aimed intracavitary position relative to the diseased portion as a result of the penetrating operation, the needle head 22b is stopped in that position and high frequency current is applied to the electrode 23 for a treatment. In this regard, since the high frequency electrode 23 is formed in an acicular shape at its fore end through which current flows, the diseased portion in contact with the electrode 23 undergoes coagulation or incision under the influence of Joule heat which is generated by the high frequency current. The feasibility of these high frequency treatments by a puncture needle, which is penetrated to a certain depth through an intracavitary wall, broadens the range of therapeutic treatments to which the ultrasound endoscope is applicable. Besides, the penetration of the puncture needle member 22 can be monitored even by way of X-ray images in which the metal electrode 23 on the needle head 22b is clearly visible as a contrast medium.

Figure 7:
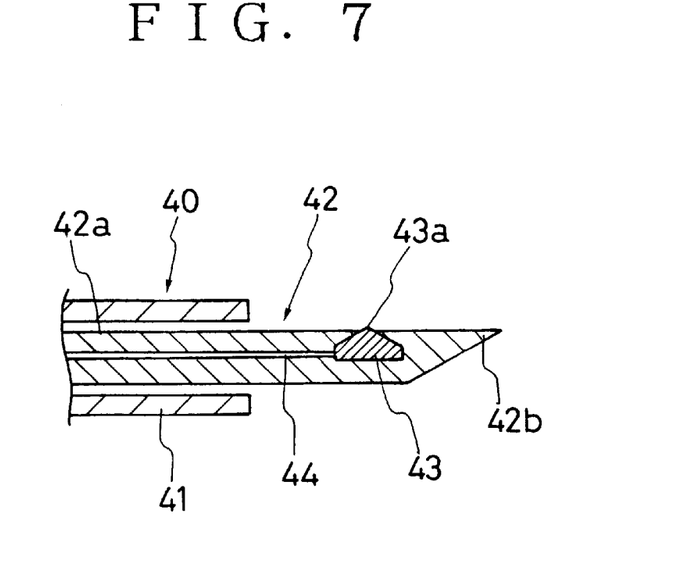
FIG. 7 is a fragmentary sectional view of a further embodiment of the puncture needle of the invention.

Referring now to FIG. 7, there is shown a further embodiment of the invention, employing a puncture instrument 40 which is the same as the foregoing embodiment in that it has a puncture needle member 42 slidably fitted in a flexible guide tube 41 of electrically insulating material. The puncture needle member 42 is constituted by an elongated flexible needle body 42a, a sharp-pointed needle head 42b which is contiguously provided at the fore end of the flexible needle body 42a, and a high frequency electrode 43 which is integrally embedded in the puncture needle member 42, with a pointed end of an acicular electrode portion 43a exposed to the outside on a lateral side of the puncture needle member 42 at a position close to the needle head 42b. A wiring cable 44 from the high frequency electrode 43 is passed through the flexible needle body 42a of the puncture needle member 42 and connected at its proximal end to a high frequency power source in the same manner as in the above-described first embodiment.

With the puncture instrument 40 of the above-described arrangements, it becomes possible to apply a high frequency treatment to wider areas around the puncture needle member 42 which has been penetrated into a diseased portion in a particular intracorporeal region, by turning the puncture needle member 42 about its axis while supplying high frequency current thereto.

Figure 8:
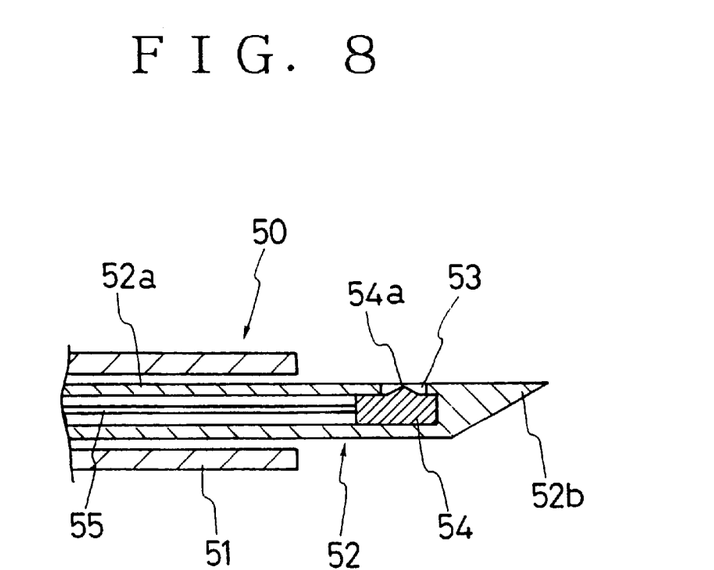
FIG. 8 is a fragmentary sectional view of a further embodiment of the puncture needle according to the invention.

Shown in FIG. 8 is a further embodiment of the invention, employing a puncture instrument 50 which is constituted by a guide tube 51 of an electrically insulating material and a puncture needle member 52 similarly of an electrically insulating material. The puncture needle member 52 is provided with a sharp-pointed needle head 52b at the fore end of a hollow tubular needle body 52a. A window 53 is opened in the hollow tubular body 52a of the puncture needle member 52 at a position close to the proximal end of the sharp-pointed needle head 52b, receiving therein a high frequency electrode 54 in such a manner as to expose an acicular electrode portion 54a through the window 53. A wiring cable 55 from the high frequency electrode 54 is passed through the hollow tubular body 52a of the puncture needle member 52. The puncture instrument of this construction is also capable of applying a high frequency treatment to a broader range of areas around the puncture needle member similarly to the above-described second embodiment.

Figure 4:
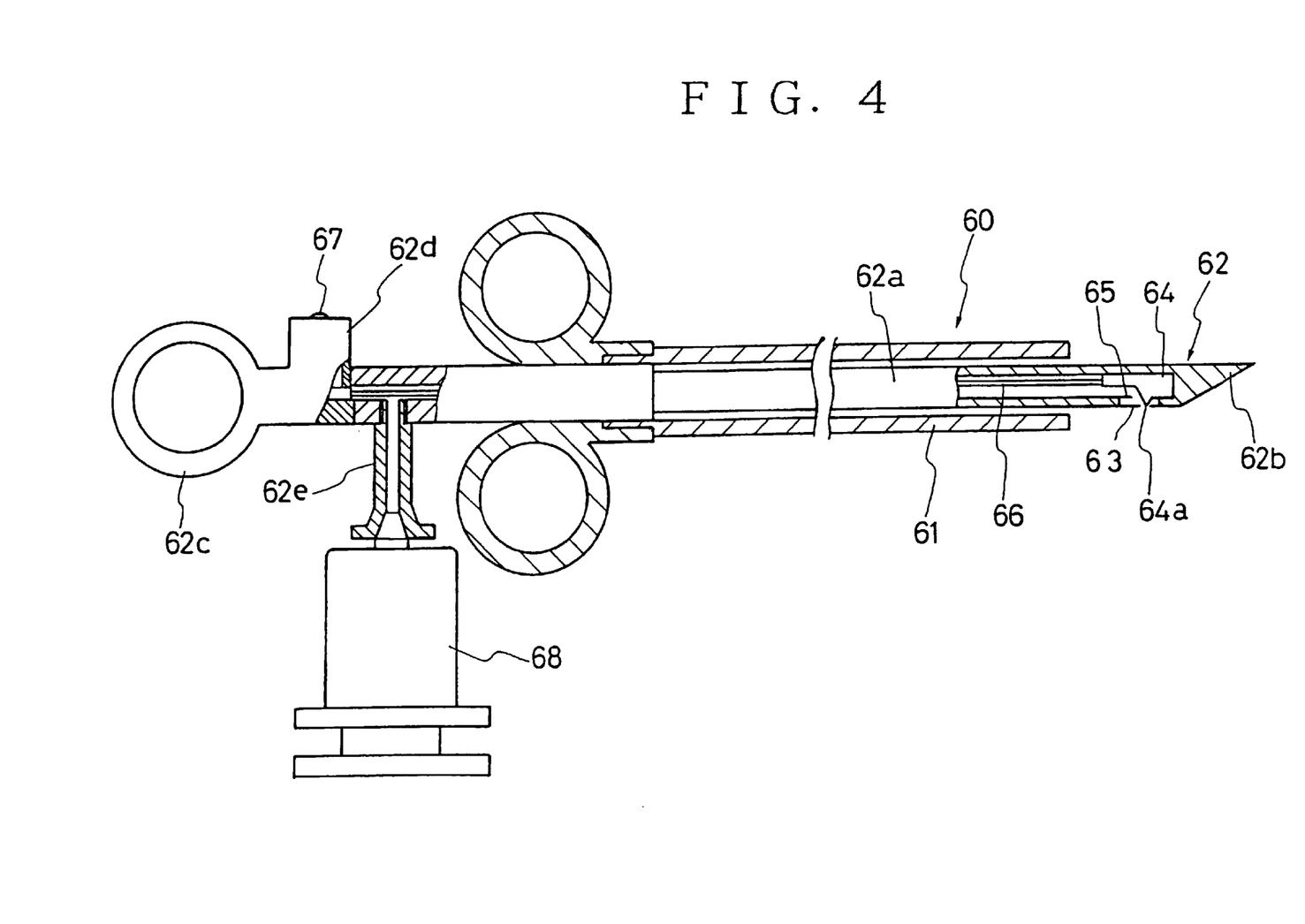
FIG. 4 is a schematic side view of one embodiment of the puncture instrument according to the invention.

Shown in FIG. 4 is a further embodiment of the invention, employing a puncture instrument 60 which is constituted by a guide tube 61 and a puncture needle member 62 similarly to the third embodiment of FIG. 8. The puncture needle member 62 is provided with a sharp-pointed needle head 62b at the fore end of a hollow tubular body 62a. A window 63 is opened on a lateral side of the tubular needle body 62a at a position close to the proximal end of the sharp-pointed needle head 62b. In this case, however, in order to use the inner hollow space of the tubular body 62a of the needle member 62 as a suctional passage, a high frequency electrode 64 with an acicular electrode portion 64a is securely fixed on the inner periphery of the tubular needle body 62a along one side thereof. The acicular electrode portion 64a is located in the window 63 in such a manner as to leave a gap space 65 therein to communicate the suctional passage in the tubular body 62a of the puncture member 62 with the outside.

The puncture needle member 62 is provided with a grip 62c also in the form of a ring at the proximal end of its hollow tubular body 62a. The wiring cable 66 from the high frequency electrode 64 is passed through the tubular needle body 62a and connected to a connector pin 67 in a connection terminal 62d at a position on the front side of the grip 62c. Although not shown in the drawing, the connector pin 67 is connectable to the output cable of a high frequency power source substantially in the same manner as in the embodiment. In this embodiment, the tubular body 62a of the needle member 62 is further provided with a suctioning port 62e on the front side of the connection terminal 62d, the suctioning port 62e having a cylindrical housing which is disconnectibly connectible to a sucking device 68 such as syringe or the like.

With the puncture instrument 60 of the above-described arrangement, in case the head portion of the puncture needle member, which has been penetrated into an intracorporeal portion, is met by a pool of exuding body fluid, for example, by bleeding as caused as a result of the needle penetration, the body fluid can be sucked out by the sucking device 68 in order to bring the high frequency electrode 64 into intimate contact with the tissues in the intracorporeal portion which needs a high frequency treatment. This makes it possible to carry out a necessary treatment in an efficient manner. The suctional passage is also useful for suctionally removing vapors which may occur at the time of a high frequency incision treatment. In this instance, of course, the puncture needle member 62 may be put in rotation about its axis during the treatment to broaden the range of the treatment areas.

Figure 10:
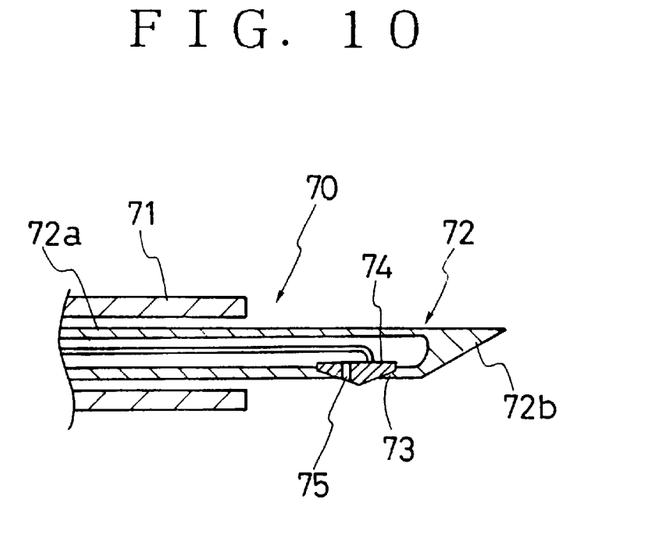
FIG. 10 is a fragmentary sectional view of a further embodiment of the puncture needle of the invention.

The suctional drainage is also feasible with a puncture needle member having a high frequency electrode arranged as in FIG. 10. More specifically, shown in FIG. 10 is a puncture instrument 70 of a modified construction, a further embodiment of the invention, having a puncture needle member 72 slidably received in a guide tube 71. A high frequency electrode 74 is fitted in a window 73 which is opened in a hollow tubular body 72a of the puncture needle member 72 close to the proximal end of its sharp-pointed needle head 72b. An aperture 75 is formed in the high frequency electrode 74 itself which covers the window 73, so that the suctional passage in the hollow tubular body 72a is opened to the outside at a position on the proximal side of the needle head 72b. The puncture instrument of this modified construction also permits suctioning of body fluid at the time of or during a high frequency treatment in a manner similar to the embodiment of FIG. 4.

Figure 11:
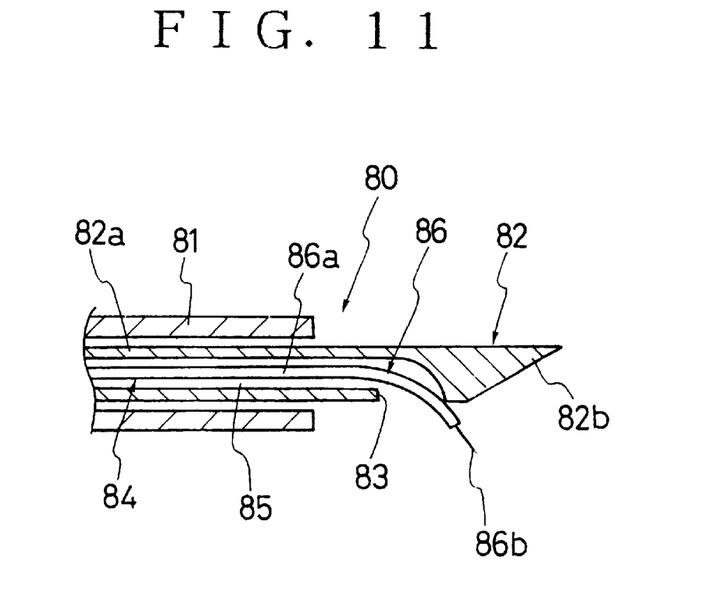
FIG. 11 is a fragmentary sectional view of a further embodiment of the puncture needle of the invention.

Referring now to FIG. 11, there is shown a puncture instrument 80 with a high frequency electrode suitable for serving as a high frequency knife. In this embodiment, the puncture instrument 80 is likewise constituted by a guide tube 81 and a puncture needle member 82 which has a window 83 opened in its hollow tubular body 82a at a position close to a sharp-pointed needle head 82b. The inner hollow space of the tubular needle body provides a guide passage 85 for a high frequency knife 84 which, as well known in the art, has an insert portion 86 having a conductor wire 86b sheathed in an insulating sleeve 86a. A tip end portion of the conductor wire 86b is protruded from the insulating sleeve 86a over a predetermined length to form an acicular electrode.

At the time of mounting the puncture instrument 80 on an ultrasound endoscope, the high frequency knife 84 is held in a retracted position within the puncture needle member 82 and the puncture instrument 80 itself is held in a retracted position within the guide tube 81. In order to use the high frequency knife 84, firstly the puncture instrument 80 is protruded from the puncture instrument guide channel 11 until the fore end of the guide tube 81 comes into abutment against an aimed intracavitary wall portion. In this state, the puncture needle member 82 is driven forward to penetrate the needle head 82b through the intracavitary wall to a depth where a high frequency incision treatment is required. Then, the high frequency knife 84 is protruded out of the window 83 in the tubular body 82a of the needle member 82, followed by energization of the conductor wire 86b to cut into a diseased portion with the high frequency knife 84. The inner hollow space of the needle member 82 of this puncture instrument 80 can also be utilized as a suctional passage.

Figure 12:
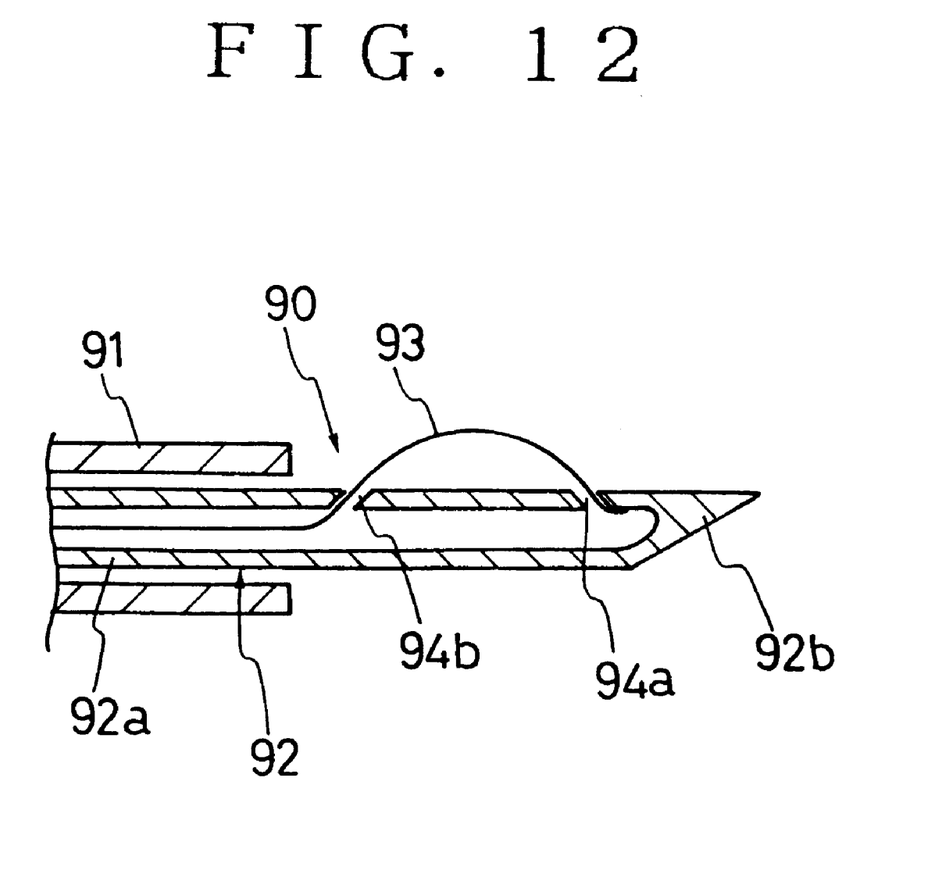
FIG. 12 is a fragmentary sectional view of a further embodiment of the puncture needle of the invention.

FIG. 12 illustrates a puncture instrument 90 which has, slidably within a guide tube 91, a puncture needle member 92 with a sharp-pointed needle head 92b at the fore end of a hollow tubular body 92a similarly to the foregoing embodiments. In this case, a conductor wire 93 is inserted in the tubular body 92a of the needle member 92, forming a linear high frequency electrode in the form of a papillotomy knife on the proximal side of the sharp-pointed needle head of the needle member 92. More specifically, the puncture needle member 92 is provided with a couple of front and rear wire threading apertures 94a and 94b in spaced positions immediately behind the sharp-pointed needle head 92b, threading the conductor wire 93 through the tubular needle body 92a and through the apertures 94a and 94b to form a papillotomy knife on the outer side of a fore end portion of the tubular needle body 92a between the apertures 94a and 94b. The conductor wire 93 is connected to a high frequency power source through a connection terminal at the proximal end of the puncture needle member 92. Accordingly, an incision treatment can be carried out on a diseased portion in an intracorporeal region by driving the puncture needle member 92 into the intracorporeal region and pulling back and forth the conductor wire 93 which is excited with high frequency current.

As clear from the foregoing description, the puncture instrument according to the present invention employs an elongated puncture needle member which is slidably fitted in a guide tube and which is provided with a sharp-pointed needle head at the fore end thereof for penetration into an intracorporeal portion of a patient, the needle member carrying an electrode for a high frequency treatment at a position immediately on the proximal side of the sharp-pointed needle head, permitting to carry out a high frequency treatment such as high frequency coagulation or high frequency incision on a diseased portion in an intracorporeal region in a safe and secure manner.

What is claimed is:

1. A puncture instrument to be introduced into a body cavity of a patient by way of an instrument channel of an ultrasound endoscope and penetrated into an intracorporeal portion for a high frequency treatment and for sucking out a body fluid under observation, which comprises:

an ultrasound scanning device for said ultrasound endoscope, said scanning device including a transducer mounted on distal end of said ultrasound endoscope;

a guide tube insertable into the body cavity of a patient through said instrument channel of said ultrasound endoscope;

a puncture needle member including
an elongated flexible body portion slidably received in said guide tube,
a puncture needle head provided contiguously at a fore end of said elongated flexible body portion,
a passage formed axially and internally through said flexible body portion of said puncture needle member and leading to an opening formed in said puncture needle head, and
a high frequency electrode provided in said puncture needle head at least in a partly exposed state and connected to a wiring cable passed through said passage, said high frequency electrode including an aperture which communicates with said passage;

a needle manipulator connected to a proximal end portion of said flexible body portion to move said puncture needle head back and forth between a retracted position within said guide tube and a protruded position extending out of said guide tube for penetration into a target intracorporeal portion to be treated; and a suction device connected to a proximal end portion of said passage to generate a suction force therein.

2. A puncture instrument as defined in claim 1, wherein said high frequency electrode is fixedly embedded in a partly exposed state on a lateral side of the fore end portion of said puncture needle member.

3. A puncture instrument as defined in claim 1, wherein said body portion of said puncture needle member has a window opening formed therein and wherein said high frequency electrode is fitted in said window opening in a partly exposed state.

4. A puncture instrument as defined in claim 1, wherein said puncture needle head comprises a sharp-pointed needle head.

5. A puncture instrument as defined in claim 1, wherein said aperture which communicates with said passage comprises a single passageway through said electrode.

6. A puncture instrument as defined in claim 1, which comprises a catheter having a flexible section, an angle section and a fore end section wherein said scanning device is positioned in said fore end section.

7. A puncture instrument as defined in claim 6, wherein said fore end section has an opening formed therein in proximity with said ultrasound scanning device and through which said puncture needle member is positionable.

8. A puncture instrument as defined in claim 7, wherein said opening is positioned in said fore end section upstream of said ultrasound scanning device.

* * * * *

UNITED STATES PATENT AND TRADEMARK OFFICE
CERTIFICATE OF CORRECTION

PATENT NO. : 6,200,313 B1
DATED : March 13, 2001
INVENTOR(S) : Kenji Abe et al.

It is certified that error appears in the above-identified patent and that said Letters Patent is hereby corrected as shown below:

Title page,
The CPA information has been omitted. It should read as follows:

-- [45] Date of Patent: *Mar. 13, 2001 --

-- [*] This patent issued on a continued prosecution application filed under 37 CFR 1.53(d), and is subject to the twenty year patent provisions of 35 U.S.C. 154(a)(2). --

Signed and Sealed this

Twentieth Day of November, 2001

*Attest:*

*Attesting Officer*

NICHOLAS P. GODICI
*Acting Director of the United States Patent and Trademark Office*